US00PP22354P2

(12) United States Plant Patent
Kordes

(10) Patent No.: US PP22,354 P2
(45) Date of Patent: Dec. 20, 2011

(54) CLIMBING ROSE PLANT NAMED 'KORDITWOL'

(50) Latin Name: *Rosa hybrida*
Varietal Denomination: KORditwol

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,245

(22) Filed: Oct. 14, 2010

(51) Int. Cl.
*A01H 5/00* (2006.01)

(52) U.S. Cl. ..... Plt./110

(58) Field of Classification Search ..... Plt./110
See application file for complete search history.

*Primary Examiner* — Kent L Bell

(57) ABSTRACT

A new and distinct variety of rose with long lasting, novel white flowers, and attractive foliage with good disease resistance. It exhibits climbing growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORditwol'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2003. The crossing was between an unnamed seedling from the same inventor and another unnamed seedling from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORditwol'.

SUMMARY OF THE INVENTION

The new rose plant may be distinguished from its seed parent, an unnamed seedling, by the following combination of characteristics:

1. Diameter of the open flower of 'KORdiwol' is 90 mm on average. Diameter of the open flower of the seed parent is 70 mm on average.
2. Common color of the flower of 'KORditowl' is white. Common color of the flower of the seed parent is red.

The new rose plant may be distinguished from its pollen parent, an unnamed seedling, by the following combination of characteristics:

1. Average height of 'KORditwol' at maturity is 250 cm. Average height of the pollen parent at maturity is 110 cm.

2. 'KORditwol' has a slight fragrance. The pollen parent has a moderate-to-strong fragrance.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORditwol' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORditwol' was selected in May, 2004 from the seedling beds to be asexually propagated for further evaluation. The first asexual propagation of 'KORditwol' was done by budding to seedling understocks in July, 2004 at the inventor's nursery in Offenseth-Sparrieshoop, Germany.

This initial and other subsequent propagations conducted in controlled environments demonstrate that 'KORditwol' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORditwol'.

DETAILED BOTANICAL DESCRIPTION

The following is a description of 'KORditwol', as observed growing in July, 2009 in a nursery in Sparrieshoop, Germany on plants of 1 year of age. Subsequent observations were made in September, 2010 at a nursery in Jackson County, Oreg. on plants of one year of age. Color references are made using The Royal Horticultural Society (London, England) Colour Chart, 2001 except where common terms of color are used.

For a comparison, several physical characteristics of the rose variety 'KORstacha', an unpatented rose variety from the same inventor are compared to 'KORditwol' in Chart 1.

CHART 1

| Characteristic | 'KORditwol' | 'KORstacha' |
|---|---|---|
| Mature height | 250 cm | 760 cm |
| Fragrance | Slight | Strong |
| Petal Count | 20-25 | 9-16 |

Parents:

*Seed parent.*—An unnamed seedling.

*Pollen parent.*—An unnamed seedling.

Classification:

*Botanical classification.*—*Rosa hybrida,* 'KORditwol'.

*Commercial classification.*—Climbing rose.

FLOWER AND FLOWER BUD

*Blooming habit.*—Recurrent.

*Flower bud.*—Size: Upon opening, 30 mm in length from base of receptacle to end of bud and 20 mm diameter at its widest point. Bud form: Medium. Pointed ovoid. Bud color: As sepals first unfold, bud color is White Group 155A sparse intonations of Orange Group 27A. When ¼ open, the upper surface of petals is White Group 155A, and the lower surface is White Group 155A. Sepals: Size: Average 20 mm long×7 mm wide. Shape: Sepals generally subulate. Sepal apex is generally cirrose. Weak foliaceous appendages on three of the five sepals. Base is flat at union with receptacle. Quantity: Five. Margins: With fine hairs and stipitate glands. Surface texture: Inner side: Covered in fine hairs. Outer surface: Smooth. Stipitate glands are present. Color: Upper surface Green Group 138C. Lower surface Yellow-Green Group 144A.

*Receptacle.*—Surface: Smooth. Glabrous. Color: Yellow-Green Group 144A. Shape: Campanulate. Size: 10 mm (h)×7 mm (w).

*Peduncle.*—Surface: Smooth. With stipitate glands. Length: 20 mm average length. Diameter: 1 mm average diameter. Color: Yellow-Green Group 144A. Strength: Moderate. Borne: Multiple flower buds per stem, generally 8 to 12.

Flower bloom: Fragrance: Light. Duration: On the plant 2-4 days. As a cut flower, 2 to 4 days. Senesced petals drop away cleanly. Size: Large flowered garden rose. When open, the average flower diameter is 90 mm and the average flower height is 30 mm. Form: Shape of flower when viewed from the side: Upon opening, upper part: Flat. Upon opening, lower part: Flattened convex. Open flower, upper part: Flat. Open flower, lower part: Flattened convex.

Color:

*Upon opening, petals.*—Outermost petals: Outer Side: White Group 155D. Inner Side: White Group 155D. Innermost petals: Outer Side: White Group 155D. Inner Side: White Group 155D.

*Upon opening, basal petal spots.*—No distinctive coloration at petal base observed.

*After opening, petals.*—Outermost petals: Outer Side: White Group 155D. Inner Side: White Group 155D. Innermost petals: Outer Side: White Group 155D. Inner Side: White Group 155D.

*After opening basal petal spots.*—No distinctive coloration at petal base observed.

General tonality: On open flower White Group 155D. No change in the general tonality at the end of the 5$^{th}$ day. Afterwards, general tonality is White Group 155A.

Petals:

*Petal count.*—Approximately 20-25 petals under normal conditions.

*Petal reflex.*—Petals reflex slightly.

*Petal edge.*—Entire.

*Petal shape.*—Rounded. Apex shape is round. Shape of base is rounded.

*Petal size.*—40 mm long; 40 mm wide.

*Thickness.*—Average.

*Petal arrangement.*—Generally in a regular pattern with overlapping edges.

Petaloids: Present.

*Petaloid count.*—Average of 3-5 per flower.

*Petaloid edge.*—Smooth.

*Petaloid texture.*—Smooth.

*Petaloid shape.*—Linear to elliptic.

*Petaloid size.*—Petaloids are 8 mm long and 6 mm wide.

*Petaloid color.*—Color of inner side is White Group 155D. Color of outer side is White Group 155D.

Reproductive organs:

*Pistils.*—Approximately 40 present. Stigmas: Location: Slightly inferior in position to anthers. Color: Yellow-Green Group 150A. Styles: Length: 8 mm long. Color: Yellow-Green Group 150C.

*Stamens.*—Approximately 80-90 on average and regularly arranged. Anthers: Size: 1 mm long. Color: Yellow-Orange Group 15A. Pollen: Generally present. Color: Yellow Group 4A. Filaments: Color: Yellow Group 4A. Length: 8 mm.

THE PLANT

*Plant growth.*—Vigorous. Erect climbing habit. When grown as a budded nursery plant the average plant height is 250 cm and the average plant width is 110 cm.

*Stems.*—Stem color: Young wood: Yellow-Green Group 144A with intonations of Gray-Red Group 178B. Older wood: Yellow-Green Group 147B with intonations of Gray-Red Group 178B. Stem surface: Young wood: Smooth. Older wood: Smooth.

*Prickles.*—Present. Incidence: 10-12 per 10 cm of stem. Size: Average length: 10 mm. Color: Immature prickles: Gray-Yellow Group 160A. Mature prickles: Gray-Red Group 181A. Senescing to Gray-Yellow Group 160B. Shape: Concave. Anthocyanin: Color Gray-Red Group 178B.

*Leaves and leaflets.*—Normally 5-7 leaflets on normal leaves in middle of the stem. Venation pattern: Pyramidal net pattern. Leaf size: 145 mm (1)×85 mm (w). Quantity: Average. Texture: Upper side of leaflet: Semi glossy. Smooth. Leathery. Under side of leaflet: Matte. Smooth. Leathery. Color, mature foliage: Upper Leaf Surface: Green Group 137A. Lower Leaf Surface: Yellow-Green Group 143A. Color, juvenile foliage: Upper Leaf Surface: Yellow-Green Group 144B. Lower Leaf Surface: Yellow-Green Group 144B. Anthocyanin intonation: Present. Location: Intonations present on juvenile leaf margins. Color: Gray-Purple Group 178A.

*Stipules.*—Size: 14 mm long. 6 mm between the tips of the stipule. Main body of stipule 6 mm in width. Shape: Elongated. Winged along middle. Stipule color: Green Group 137A. Presence of stipitate glands: Present on margins. Margins: Serrated. With stipitate glands.

*Petiole.*—Length: 20 mm. Diameter: 2 mm. Petiole color: Gray-Red Group 178A. Anthocyanin present on juvenile tissue. Underneath: A few small prickles underneath. Stipitate glands: Limited numbers of stipitate glands on margins.

*Petiole rachis.*—Length: 55 mm. Diameter: 1.5 mm. Color: Red Group 178A. Anthocyanin present on juvenile tissue. Margins: With stipitate glands. Prickles: A few small prickles underneath. Stipitate glands: Limited numbers of stipitate glands on margins.

*Leaflets.*—Size: Average size of the terminal leaflet is 60-65 mm (1)×30-35 mm (w). Shape: Elongated. Base: Ovate. Apex: Acute. Margins: Serrated. Texture: Leathery.

Hips/seed formation: Observed. Size: 10 mm(1)×10 mm(w). Color: Yellow-Green Group 144A.

Winter hardiness: To date, the variety has been grown successfully in Zone 5.

Disease resistance: Very good resistance to Powdery mildew (*Sphaerotheca pannosa*), rust (*P. disciflorum*), and blackspot (*Diplocarpon rosae*) diseases under normal growing conditions.

I claim:

1. A new and distinct variety of rose plant, as described and illustrated herein.

* * * * *

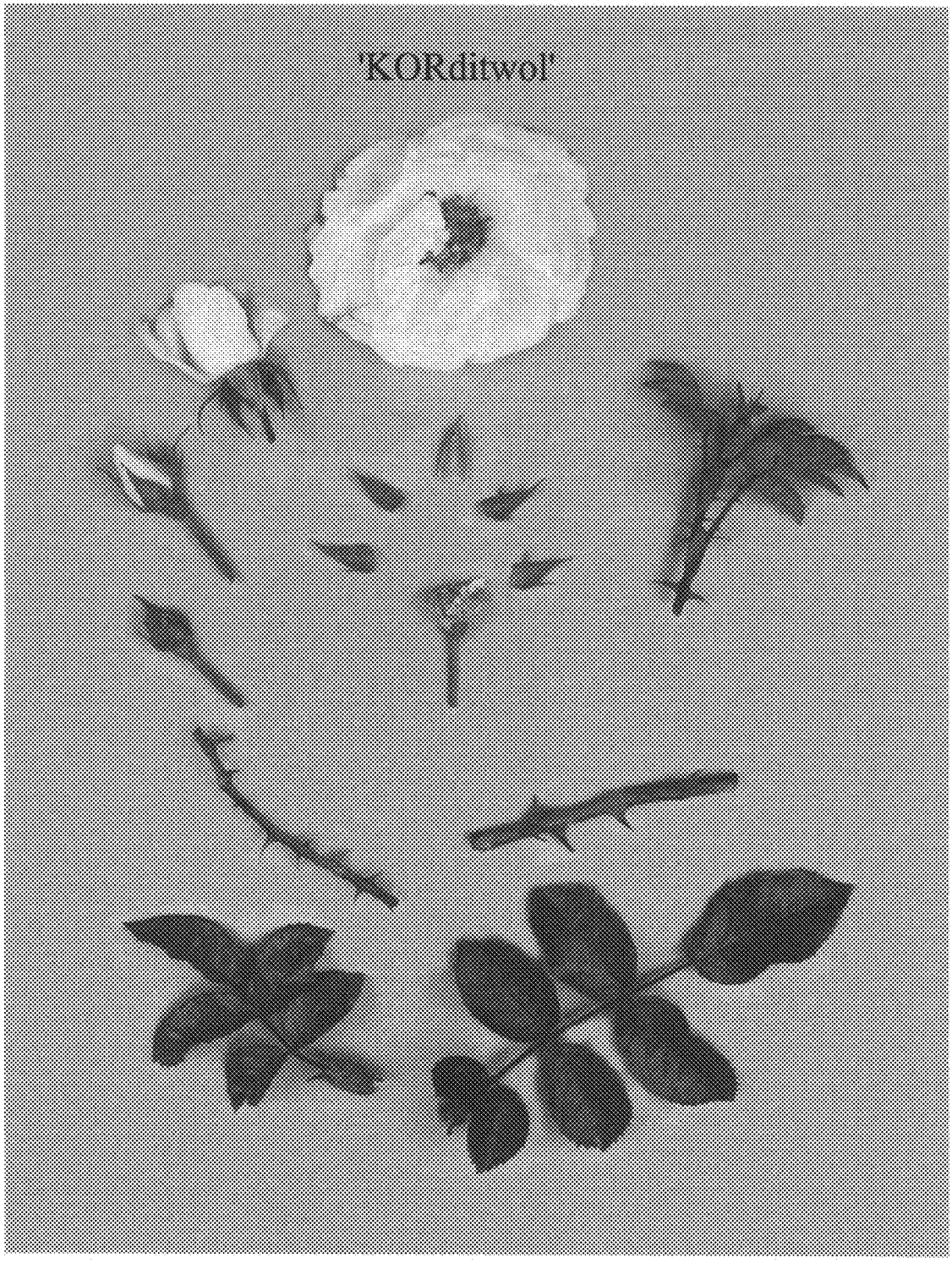
'KORditwol'